US010424091B1

(12) United States Patent
Simeoni et al.

(10) Patent No.: US 10,424,091 B1
(45) Date of Patent: Sep. 24, 2019

(54) BEAMFORMING FOR TOMOGRAPHIC DETECTION SYSTEMS

(71) Applicant: International Business Machines Corporation, Armonk, NY (US)

(72) Inventors: Matthieu Simeoni, Lausanne (CH); Paul Hurley, Oberrieden (CH); Lucien Roquette, Paris (FR); Sepand Kashani, Geneva (CH)

(73) Assignee: Internationl Business Machines Corporation, Armonk, NY (US)

( * ) Notice: Subject to any disclaimer, the term of this patent is extended or adjusted under 35 U.S.C. 154(b) by 0 days.

(21) Appl. No.: 15/939,465

(22) Filed: Mar. 29, 2018

(51) Int. Cl.
*G06T 11/00* (2006.01)
*G01T 1/10* (2006.01)
*G16H 30/20* (2018.01)

(52) U.S. Cl.
CPC .............. *G06T 11/006* (2013.01); *G01T 1/10* (2013.01); *G16H 30/20* (2018.01)

(58) Field of Classification Search
USPC ........................................................ 250/362
See application file for complete search history.

(56) References Cited

U.S. PATENT DOCUMENTS

| 2013/0188832 A1 | 7/2013 | Ma et al. |
| 2016/0157828 A1 | 6/2016 | Sumi et al. |
| 2017/0156698 A1 | 6/2017 | Park et al. |

*Primary Examiner* — Edwin C Gunberg
(74) *Attorney, Agent, or Firm* — Scully, Scott, Murphy & Presser, P.C.; Daniel P. Morris, Esq.

(57) ABSTRACT

A method of beamforming datasets from a tomographic detection system. The system comprises scintillation detectors that are arranged in D detector pairs, $D \geq 1$, wherein the detectors are adapted to count radiation hits. According to the method in one aspect, a tomographic dataset is received for each detector pair coordinates $(\theta_d, p_d)$ of a detector pair d of the D detector pairs, so as to obtain a plurality of tomographic datasets. Each of said datasets is associated with respective detector pair coordinates $(\theta_d, p_d)$. Then, for each point y of interest, the received datasets are coherently combined by weighting the datasets according to respective beamforming weights $w_d(y) = \omega(\theta_d, p_d; y)$, based on said respective detector pair coordinates $(\theta_d, p_d)$ and coordinates of said each point y of interest. This way, a signal focusing on said each point y is obtained. Related tomographic detection systems and computer program products may be also presented.

20 Claims, 10 Drawing Sheets

BEAMFORMING FOR TOMOGRAPHIC DETECTION SYSTEMS

BACKGROUND

The present disclosure relates in general to the field of tomographic detection methods and signal reconstructions methods, as well as to related detection systems. In particular, it is directed to methods that coherently combine detection signals thanks to beamforming weights judiciously adapted to the context of tomography, to obtain signals focusing on points of interest.

Focused beamformers have been extensively used in phased-array signal processing, leading to simple and efficient imaging procedures, with high sensitivity and resolution. Such beamformers coherently combine networks of antennas to achieve a radiation pattern, also called array beamshape, with high directivity. This beamshape acts as a Dirac-like spatial filter, which makes it possible to scan the incoming signal for particular locations. This imaging procedure is called imaging by beamforming (or B-scan) and is used in several applications of phased-array signal processing, which include radio astronomy, ultrasound imaging, sonars and radars, wireless networks and sound localization. Phased-array signal processing is, so far, exclusively concerned with the estimation of wavefields (acoustic or electro-magnetic).

Besides, tomographic detection systems such as positron emission tomography (PET) are known, which provide medical imagery techniques that are notably used to observe metabolic processes in the human body (e.g., it allows the metabolic activity of an organ to be reconstructed). PET scanners comprise a number of scintillation detectors arranged in a ring structure, which detectors sense annihilation photons produced from the positron emission decay of a radioactive tracer injected into a living subject. Various 2D or 3D reconstruction techniques have been proposed. Yet, PET imaging methods mostly rely on the so-called filtered back projection (FBP) methods.

SUMMARY

According to a first aspect, the present invention is embodied as a method of beamforming datasets from a tomographic detection system. The system comprises scintillation detectors that are arranged in D detector pairs, D≥1, wherein the detectors are adapted to count radiation hits. According to the method, a tomographic dataset is received (e.g., at a suitable processing module and following a detection process) for each detector pair coordinates $(\theta_d, p_d)$ of a detector pair d of the D detector pairs, so as to obtain a plurality of tomographic datasets, where each of said datasets is associated with respective detector pair coordinates $(\theta_d, p_d)$. Then, for each point y of interest, the received datasets are coherently combined by weighting the datasets according to respective beamforming weights $w(y)=\omega(\theta_d, p_d; y)$, based on said respective detector pair coordinates $(\theta_d, p_d)$ and coordinates of said each point y of interest, where c can be regarded as a function of both $(\theta_d, p_d)$ and y. This way, a signal focusing on said each point y is obtained.

According to another aspect, the invention can be embodied as a tomographic detection system, wherein the system comprises scintillation detectors arranged in D detector pairs, D≥1, the detectors adapted to count radiation hits. The system further comprises a reconstruction module, in data communication with the detectors. The module is configured for receiving a tomographic dataset, for each detector pair coordinates $(\theta_d, p_d)$ of a detector pair d of the D detector pairs, so as to obtain a plurality of tomographic datasets, each associated with respective detector pair coordinates $(\theta_d, p_d)$. The module is further configured to coherently combine, for each point y of interest, the received datasets by weighting the latter according to respective beamforming weights $w(y)=\omega(\theta_d, p_d; y)$, based on said respective detector pair coordinates $(\theta_d, p_d)$ and coordinates of said each point y of interest, so as to obtain a signal focusing on said each point y.

According to a final aspect, the invention can be embodied as a computer program product for beamforming datasets from a tomographic detection system such as described above. The computer program product comprising a computer readable storage medium having program instructions embodied therewith, the program instructions executable by one or more processors, to cause to implement steps according to the method described above.

Devices, apparatuses, systems, computerized methods and computer program products embodying the present invention will now be described, by way of non-limiting examples, and in reference to the accompanying drawings.

BRIEF DESCRIPTION OF SEVERAL VIEWS OF THE DRAWINGS

The accompanying figures, where like reference numerals refer to identical or functionally similar elements throughout the separate views, and which together with the detailed description below are incorporated in and form part of the present specification, serve to further illustrate various embodiments and to explain various principles and advantages all in accordance with the present disclosure, in which:

FIG. 2A depicts a PSF as obtained in embodiments, whereas the PSF shown in FIG. 2B was obtained with a known filtered back projection algorithm.

FIGS. 3A, 3B and 3C respectively depict: a rectangular ramp filter function (FIG. 3A); a corresponding function $1_{rec}(\tilde{p})$ (FIG. 3B), from which a beamforming function $\omega_{rec}(\theta, p; y)$ can be obtained by substituting $\tilde{p}$ with $p - \langle y, \xi_\theta \rangle$ in $1_{rec}(\tilde{p})$; and a density plot of a corresponding beamshape (FIG. 3C, obtained with a rectangular window). The focus point is indicated by a white, square marker; and FIGS. 3D, 3E and 3F similarly depict: a triangular ramp filter function (FIG. 3D); a corresponding function $1_{tri}(\tilde{p})$, FIG. 3E, associated with beamforming function $\omega_{tri}(\theta, p; y)$; and a density plot of a corresponding beamshape (FIG. 3F), the focus point is again indicated by a white, square marker;

Figure 4A:
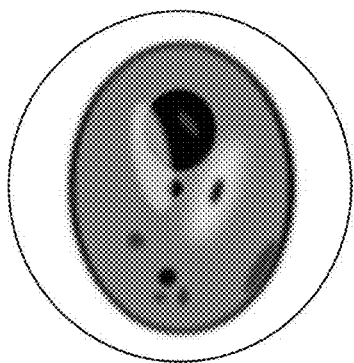
FIGS. 4A-4I compare imaging results (density plots) obtained according to embodiments (FIGS. 4A-4F) with results obtained with a known filtered back projection algorithm (FIGS. 4G-4I), based on simulated Poisson data, for D=31125 unique detector pairs (or detector tubes). In detail.
Figure 4B:
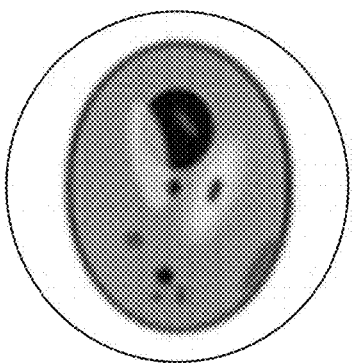
Figure 4C:
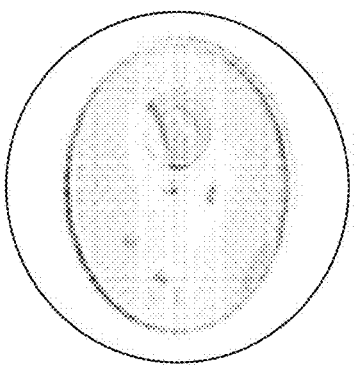
Figure 4D:
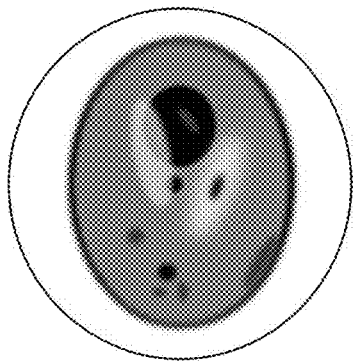
Figure 4E:
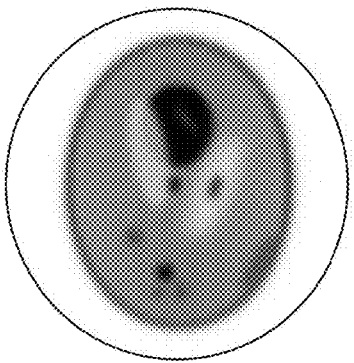
Figure 4F:
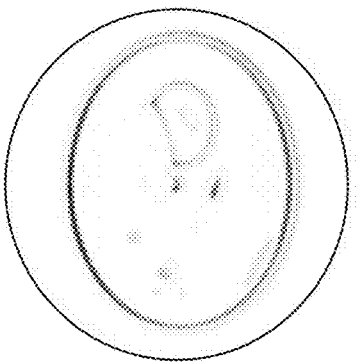
Figure 4G:
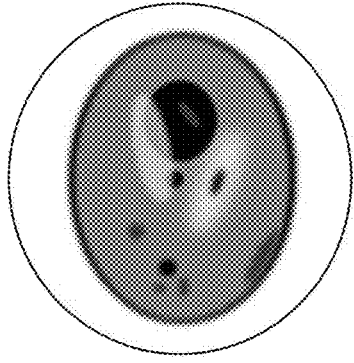
Figure 4H:
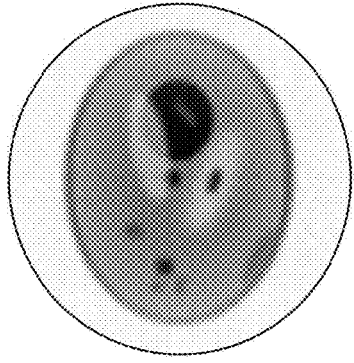
Figure 4I:
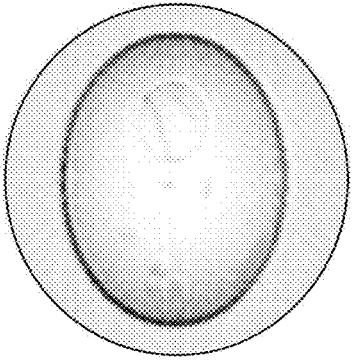
Figure 5A:
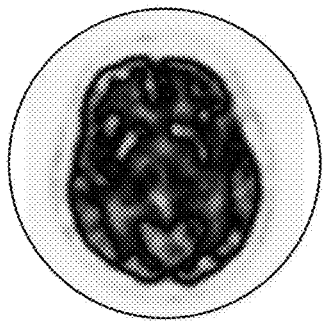
Figure 5B:
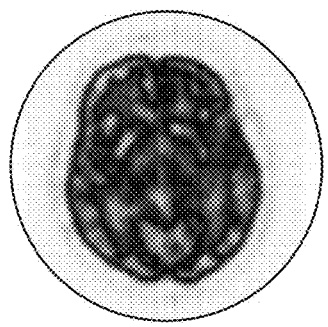
Figure 5C:
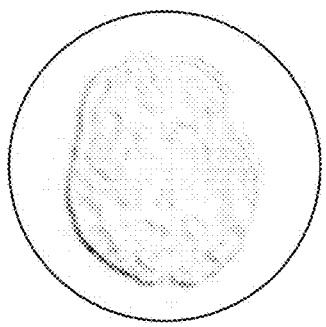
Figure 5D:
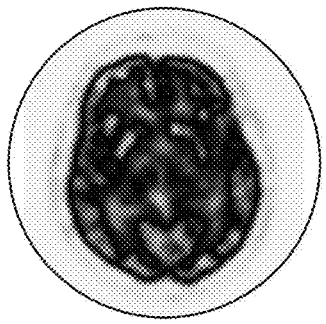
Figure 5E:
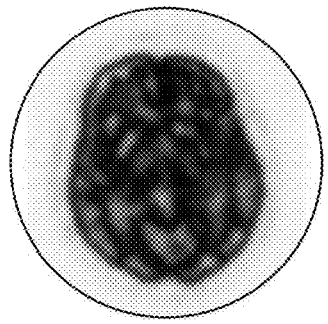
Figure 5F:
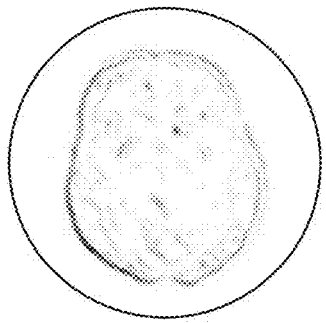
Figure 5G:
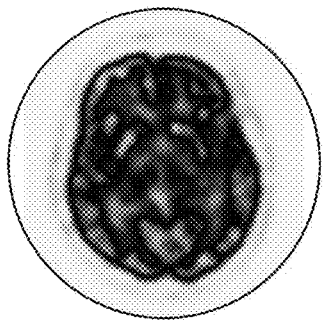
Figure 5H:
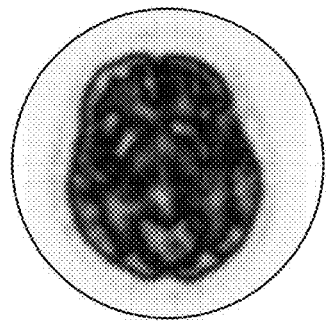
Figure 5I:
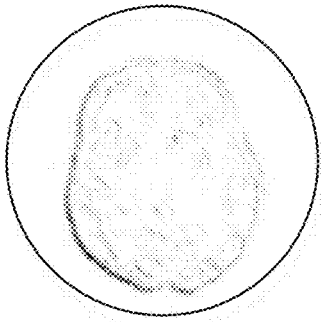
Figure 5J:
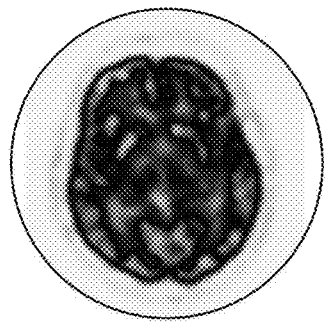
Figure 5K:
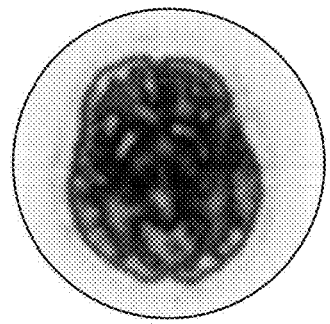
Figure 5L:
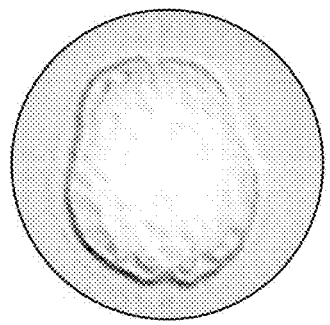
Figure 6A:
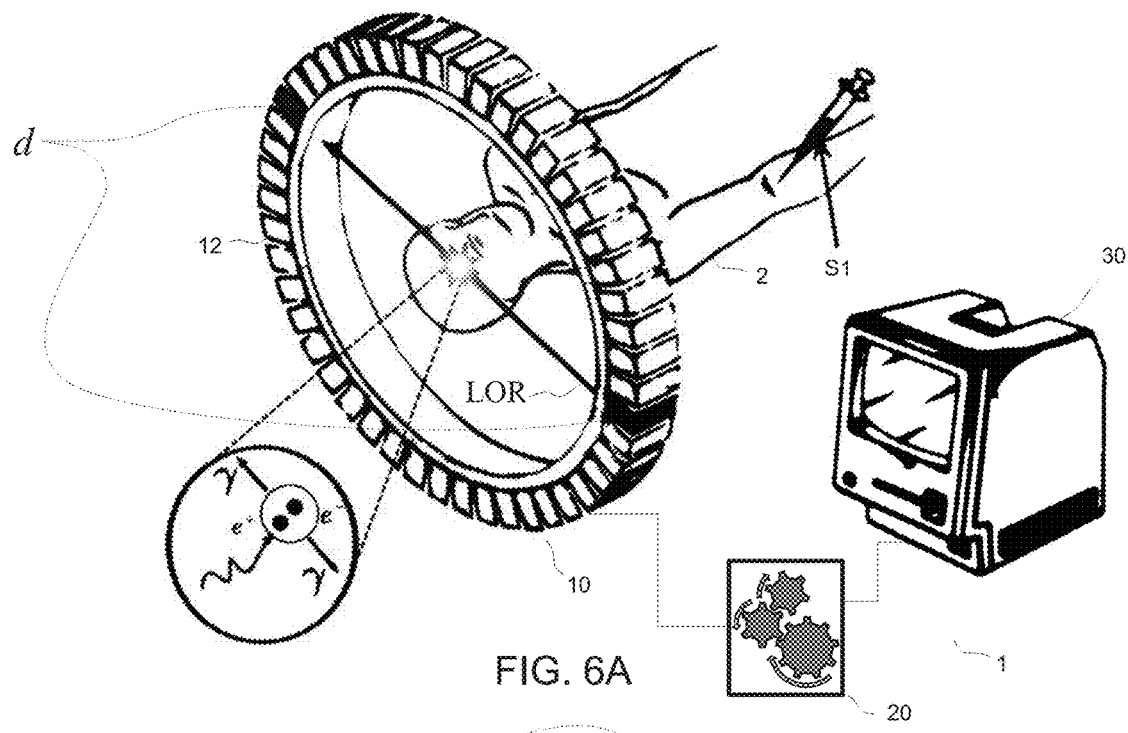
Figure 6B:
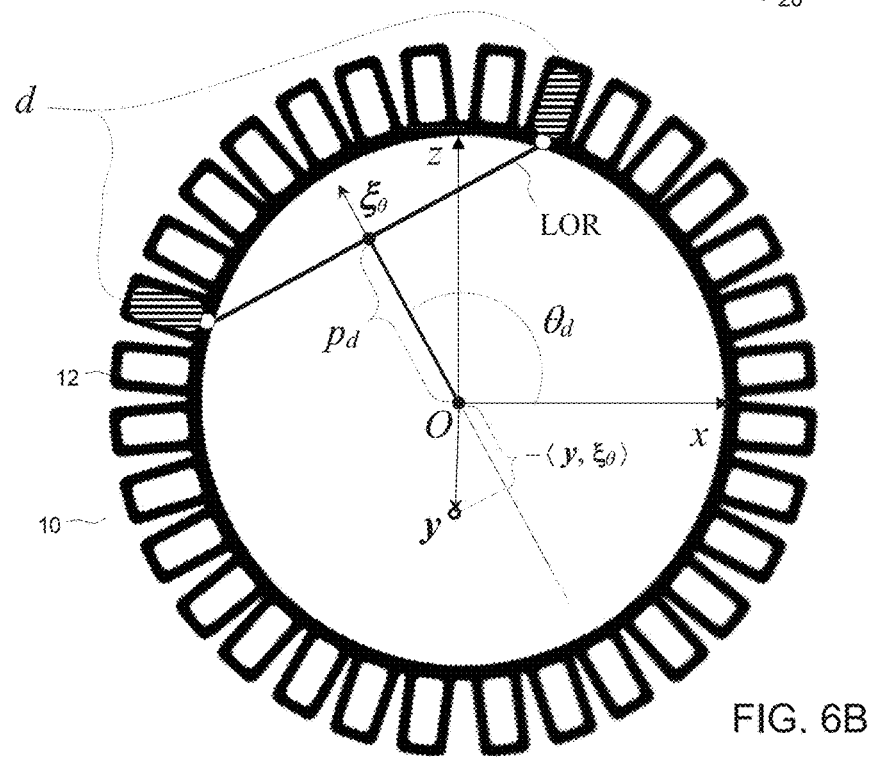
Figure 7A:
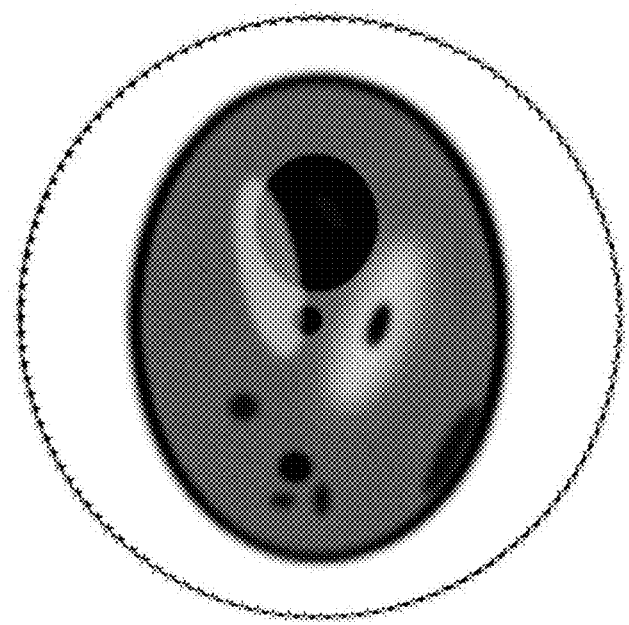
Figure 8A:
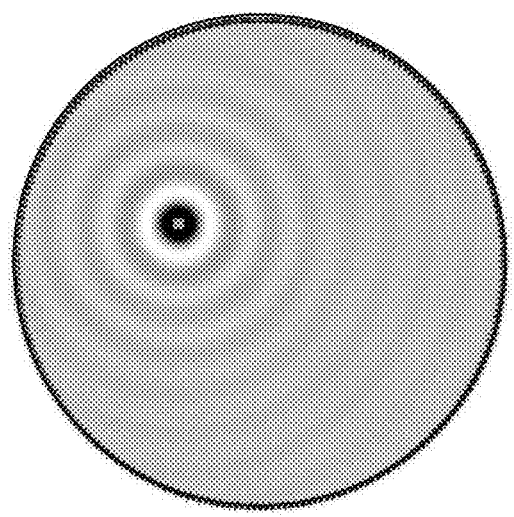
Figure 8B:
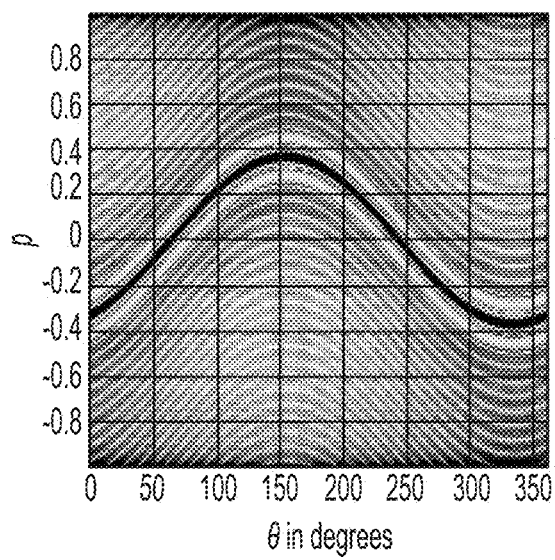

The left-hand side column (FIGS. 4A, D and G) shows the same, ground truth artificial image, purposely designed by the inventors for comparison purposes;

Images in the middle column (FIGS. 4B, E and H) were obtained by reconstruction, according to a rectangular window (FIG. 4B, according to embodiments), a triangular window (FIG. 4E, according to embodiments), and a known, filtered back projection algorithm (FIG. 4H); and Images in the right-hand side column (FIGS. 4B, E and H) depict the absolute errors (as density plots) obtained in each case;

FIGS. 5A-5L again compare imaging results (density plots) obtained according to embodiments (FIGS. 5A-5I) with results obtained with the filtered back projection algorithm (FIGS. 5J-5L), based on simulated Poisson data (D=31125). In detail:

The left column (FIGS. 4A, D, G and J) shows the same, ground truth image of a human brain, chosen for comparison purposes;

Images in the middle column (FIGS. 5B, E, H and K) were obtained by reconstruction, respectively using: a rectangular window (with $f_0$=20, FIG. 5B, according to embodiments); a triangular window ($f_0$=20, FIG. 5E, according to embodiments); a triangular window with another choice of bandwidth parameter ($f_0$=40, FIG. 5H, according to embodiments), and the filtered back projection algorithm (FIG. 5K); and Images in the right-hand side column (FIGS. 5B, E, H and L) depict the absolute errors (as density plots) obtained in each case;

FIG. 6A schematically represents a positron-emission tomography (PET) detection system comprising a ring arrangement of detector pairs, according to embodiments, and suited for implementing method steps as also involved in embodiments of the invention. FIG. 6B shows a front view of another possible ring arrangement of detector pairs, illustrating the geometry of the detectors and quantities relied upon in embodiments;

FIG. 7A shows the same, ground truth (artificial) image as shown in the left-hand side column of FIGS. 4A-4I and FIG. 7B shows a corresponding sinogram, whereby each detector tube (line-of-response), PET measurement is represented by a scatter point ($\theta_d$, $p_d$, $n(\theta_d, p_d)$) in the polar plane, having a size and color (here gray-level) proportional to the hit counts $n(\theta_d, p_d)$ recorded by the detection pair d;

FIGS. 8A and 8B show an example of beamforming weights (FIG. 8B) and the associated beamshape b(x), FIG. 8A, as used to coherently combine detection signals, as involved in embodiments. The focus point y is marked by a small square visible in the beamshape in FIG. 8A.

Figure 9A:
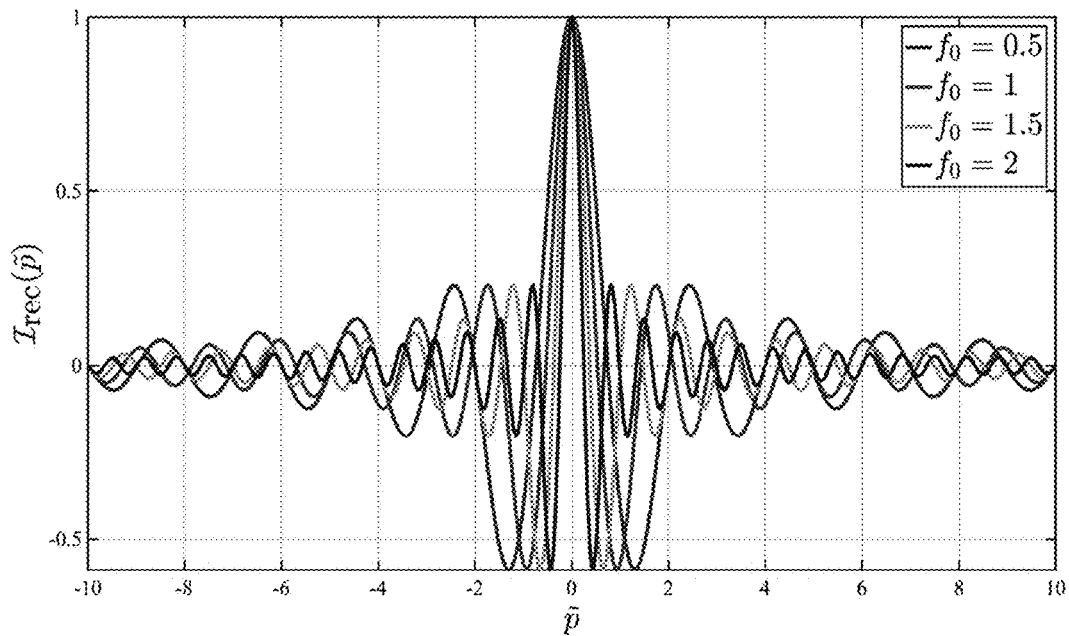
Figure 9B:
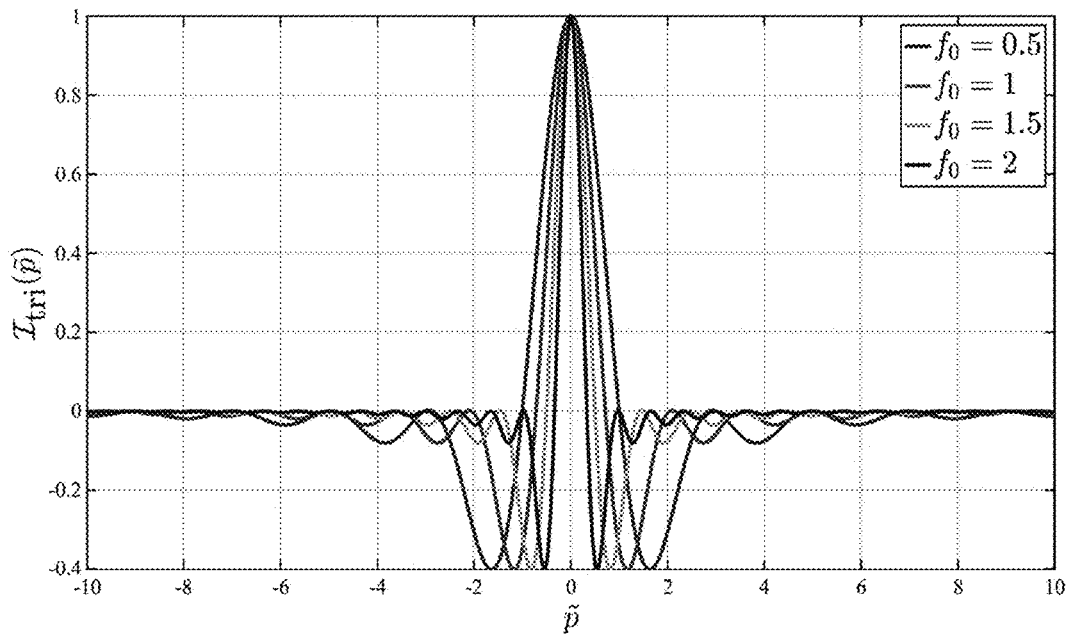
Figure 10:
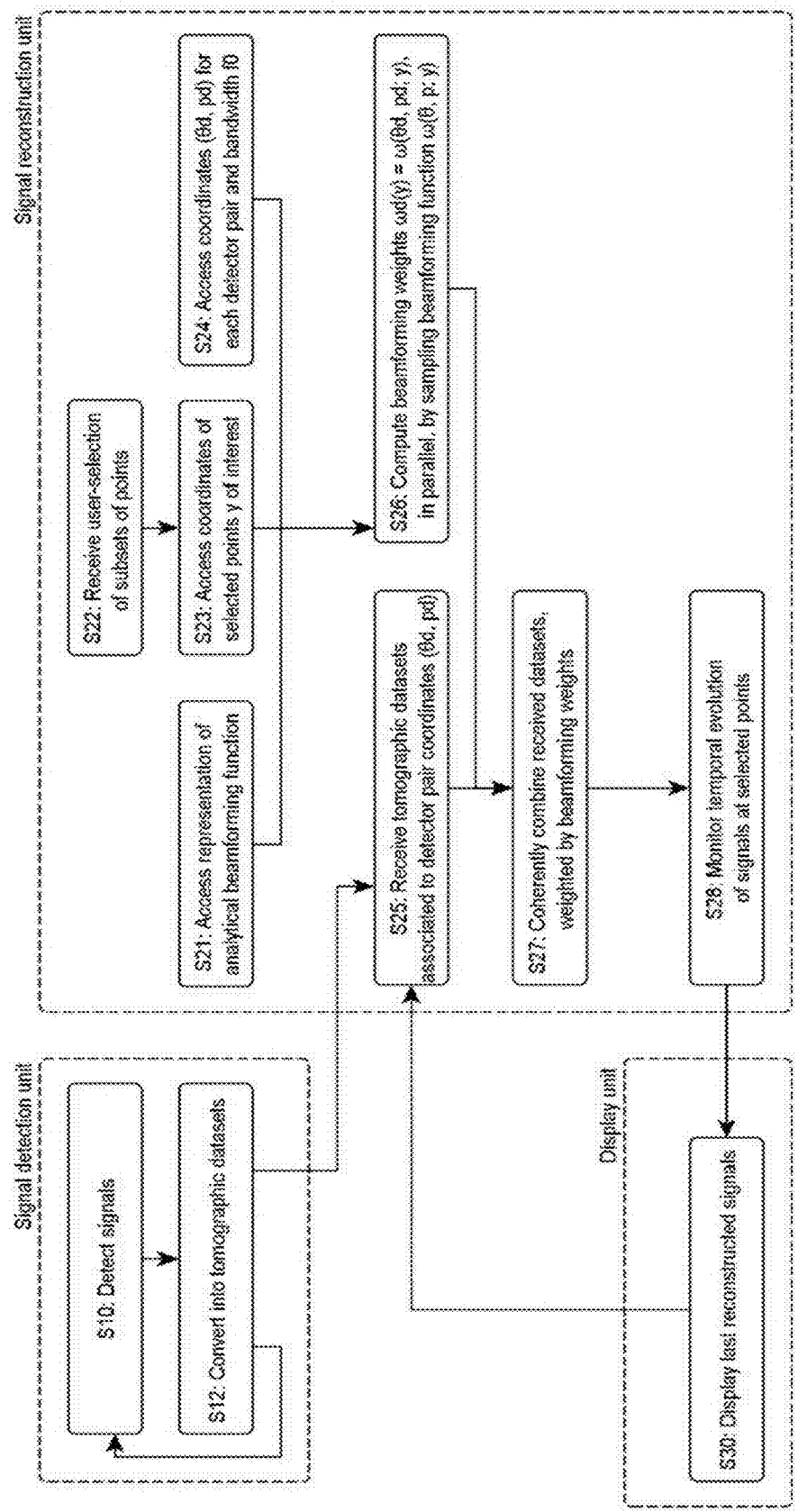

FIGS. 9A and 9B are plots representing the normalized functions $1_{rec}(\tilde{p})$ and $1_{tri}(\tilde{p})$ for various values of $f_0$, as involved in embodiments. In each case, the main lobe becomes narrower and wigglier sidelobes form as $f_0$ increases; and FIG. 10 is a flowchart illustrating high-level steps of a method of beamforming datasets from a tomographic detection system, in some embodiments.

The accompanying drawings show simplified representations of devices or parts thereof, as involved in embodiments. Technical features depicted in the drawings (particularly in FIGS. 6A and 6B) are not necessarily to scale. The number of detectors shown is purposely limited, for simplicity. Gray-level contrasts in the density plots of FIGS. 2A-2C-5A-5L, 7A-7B and 8A-8B were inverted, for the sake of depiction. Similar or functionally similar elements in the figures have been allocated the same numeral references, unless otherwise indicated.

DETAILED DESCRIPTION OF EMBODIMENTS OF THE INVENTION

The following description is structured as follows. First, general embodiments and high-level variants are described (sect. 1). The next sections address more specific embodiments and technical implementation details (sect. 2 and 3).

1. General Embodiments and High-Level Variants

In reference to FIGS. 6A-6B, 10, aspects of the invention are now described, which concerns both a method of beamforming datasets from a tomographic detection system 1 and the detection system 1 itself.

The system 1 is assumed to comprise scintillation detectors 12 arranged in D detector pairs, where D≥1, as illustrated in FIGS. 6A-6B. Each of the detectors is adapted to count radiation hits. Such detectors are known per se. Altogether, they form a detection unit 10. The tomographic detection system may for example be configured as a positron emission tomography (PET) detection system, an X-ray computed tomography scan (CT scan) system or an ultrasound tomography detection system. The system further comprises a reconstruction module 20 (FIG. 6A), suitably connected to the detection unit 10 and configured so as to allow implementation of method steps as described below.

In operation of the system 1, and according to the present methods, the signal acquisition S10-S12 gives rise to tomographic datasets. Each tomographic dataset received by the module 20 (see step S25 of the flowchart of FIG. 10) corresponds to a given detector pair d from the D pairs. A dataset essentially comprises a hit count, or a related quantity, though additional data may be provided. Each dataset received S25 can further be related to corresponding detector pair coordinates ($\theta_d$, $p_d$) of this detector pair d. Such coordinates are not necessarily fixed, as discussed below. In all cases, the module 20 receives S25 and processes S27-S28 a plurality of tomographic datasets, which are associated with respective (and distinct) detector pair coordinates ($\theta_d$, $p_d$).

According to the present methods, the received datasets are furthermore coherently combined S27, spatially, and, this, for each pointy of interest. Such points may altogether span an array of points, as usual in imaging applications, or in fact restrict to a selection of one or more points, as per user inputs received at step S22.

The coherent combination step S27 is performed by weighting the datasets (i.e., the associated hit counts) according to respective beamforming weights $w_d(y)=\omega(\theta_d, p_d; y)$, i.e., by linearly combining radiation hit counts recorded by the detector pairs, weighted by respective beamforming weights, carefully adapted to the present context. The beamforming weights are much preferably independent from the detection data received, as discussed later. Rather, the beamforming weights are here obtained based not only on coordinates of the points y of interest, but also on detector pair coordinates ($\theta_d$, $p_d$) that respectively corresponding to the datasets processed. A set of two independent coordinates is required per detector pair. In a polar coordinate system, these are the orientation angle of the pair and a radius, as discussed later in detail, in reference to FIG. 6B. Eventually, this makes it possible to obtain S30 a signal focusing on given point y. Yet, 2D imaging can be achieved by scanning over a 2D set of points y, e.g., a grid of points.

Depending on the detection system at hand, the detector pair coordinates ($\theta_d$, $p_d$) may vary throughout the detection steps S10, or not. Such coordinates vary where the system involves moving detectors. A minima, one detector pair is required. Preferably yet, several detector pairs are involved, which have respective, fixed coordinates, as in a PET detection system such as depicted in FIGS. 6A-6B.

In all cases, the beamshape can be steered by linearly combining radiation hit counts recorded by the detector pair(s), weighted by the computed beamforming weights. Computationally speaking, this is typically achieved by way of common matrix operations. Thanks to the coherent (weighted) combination of the datasets, signals associated to particular detector pairs (or pair coordinates) experience constructive interference while others experience destructive interference. The coherent signal obtained steers toward a point y of interest and, more precisely, focuses on said point, thanks to suitably computed beamforming weights, which further depend on the geometry of the detection pairs.

Note that, although the operations performed herein evoke typical beamforming operations (i.e., delays and sum operations), such operations need not involve time delays (as in delays and sum operations of typical beamforming processes), inasmuch as spatial information only need be linearly combined. In addition, the spatial filtering is here constrained by the particular geometry of the detector pair coordinates ($\theta_d$, $p_d$) and the coordinates of the point y of interest.

Again, although the steps described in this section mostly aim at obtaining a signal focusing on a single point y, this does not prevent 2D imaging, inasmuch as the same procedure can be repeated by scanning over a grid of point, thanks to the efficiency of the algorithms proposed herein.

The present methods and systems can for instance be used to estimate an organ's metabolic activity at specific physical locations. The data eventually obtained are such that they filter the original data to extract local information about the regions surrounding the selected focus points. The present approach allows better resolution and contrast to be obtained, compared with known methods, as demonstrated by simulations performed by the Inventors and discussed in detail in sect. 2.

In preferred embodiments, images are formed S30 by scanning over a grid of points and the beamforming weights are sampled from a continuous beamforming function associated with a continuous detector ring. All this is now explained in detail, in reference to particular embodiments of the invention.

To start with, the beamforming weights $w_d(y) = \omega(\theta_d, p_d; y)$ are preferably computed S26 by sampling a beamforming function $\omega(\theta, p; y)$, as evoked just above. I.e., for each distinct set of values of the variables ($\theta$, p; y), the same beamforming function $w(\theta, p; y)$ is relied on, which is sampled according to the values of $\theta$, p pertaining to the datasets received S25 and the relevant value(s) of y. This way, the desired weights $\omega(\theta_d, p_d; y)$ are obtained. After sampling S26, the computed weights are used to coherently combine S27 the datasets. The beamforming function may for instance be numerical, analytical, implicit, or otherwise be defined by a computational process, etc.

If possible, the weights may advantageously be precomputed for all potential values of $\{\theta, p; y\}$, in the interest of efficiency. Preferably, the beamforming weights are independent from the tomographic datasets obtained S25. The beamforming weights may for instance be computed S26 in parallel on a plurality of points y of interest. In addition, the weights can be computed in parallel to the data acquisition S10, S12. In all cases, since the weights do not depend to the detected signals, the resulting imaging algorithm can be made extremely efficient.

Interestingly, the present Inventors have realized that the beamforming function may initially be devised as a function (noted $1(\tilde{p})$) of the reduced distance $\tilde{p} = p - \langle y, \xi_\theta \rangle$. That is, the reduced distance $\tilde{p}$ is equal to the radial coordinate p of the detector pair coordinates ($\theta$, p) minus the projection $\langle y, \xi_\theta \rangle$ of a point y of interest on the radial direction, as illustrated in FIG. 6B for a particular detector pair d. In more detail, in a polar coordinate system, the detector pair coordinates ($\theta$, p) involve: (i) the angle $\theta$ of orientation of the line (also called line-of-reference, or LOR) joining the pair of detectors; and (ii) the minimal distance p of this line from the center of the scan field of the detectors 12. I.e., the minimal distance p is measured along the radial direction defined by $\xi_\theta$, which vector is normal to the LOR.

Considering the reduced distance $\tilde{p} = p - \langle y, \xi_\theta \rangle$ amounts to shift the transverse distance p of each detection pair according to coordinates of a point of interest, along the polar direction $\xi_\theta$ of the radius p, which lends itself well to extricate constructive interferences. Thus, each of the computed weights may, on the one hand, be independent from the signal data received and, on the other hand, solely depend on (polar) coordinates of the LOR of a detector pair and coordinates of y.

Preferably, the beamforming function is analytically defined, for computational efficiency and, this, for each potential value of the reduced distance. The beamforming function may notably be devised so as to be continuous about $\tilde{p} = p - \langle y, \xi_\theta \rangle = 0$.

Interestingly, the variable/may be taken as the conjugate variable of the argument f of the ramp filter function $\hat{h}(f)$ of the tomographic detection system, from which the beamforming function derives. For example, the beamforming function is preferably derived from a windowed version of the ramp filter function $\hat{h}(f)$, which corresponds to a Dirac delta function, so as to act as a spatial filter, scanning the intensity of the incoming signal for particular locations y.

As illustrated through various examples in sect. 2, the amplitude of the beamforming function may for instance be determined by the window size, i.e., the bandwidth $f_0$ of the detection system 1, having inverse dimensions with respect to p. For example, the beamforming function used may be derived from a band-limited ramp filter function h of the tomographic detection system 1, which function is, in the Fourier domain, suitably truncated (or windowed) according to the window size $f_0$ of the detection system. That is, the ramp filter function may be written as $\hat{h}(f) := |f| \chi(f \leq f_0)$, for some $f_0 \geq 0$, where $\chi(f \leq f_0)$ is a conveniently chosen window function. In that respect, we note that the resolution performance will be proportional to the window size $f_0$. The beamforming function is obtained by taking shifts of the Fourier transform of the ramp filter function, using $\tilde{p}$ as the conjugate variable off. From the definition of $\hat{h}(f)$, one may realize that a suitable choice of $\chi(f)$ makes it possible to obtain the beamforming function as an analytical function.

The window function $\chi$ may for instance be devised as a rectangular window function, a triangular window function or, still as Welch window function, for example. In variants, Gaussian-like window functions can be contemplated.

In PET-like tomographic detection systems, the detection units comprise a plurality of detector pairs (i.e., $D \geq 2$), where each pair d has fixed detector pair coordinates ($\theta_d$, $p_d$). In that case, each datasets received S25 by the reconstruction module 20 corresponds to fixed detector pair coordinates $(\theta_d, p_d)$ that correspond to a respective geometry of a detector pair d. In addition, in such systems, the detectors 12 may typically have a ring arrangement, as illustrated in FIGS. 6A-6B.

With such a configuration, the beamforming weights $w^*_d(y)=\omega(\theta_d, p_d; y)$ can be computed S26 by sampling the beamforming function $\omega(\theta, p; y)$ according to the fixed detector pair coordinates $(\theta_d, p_d)$ and the coordinates of the points y of interest. The points y may for instance be interactively selected by an operator (e.g., by touching or otherwise selecting an area on the display device 30, thanks to any suitable haptic device) and, upon receiving a new selection S22 of y, the module 20 may recompute the beamforming weights, as necessary to coherently combine S27 datasets. The datasets may actually be received S25 on-the-fly, as detection takes place, or be first acquired (during prior detection steps) and then appropriately stored for post-processing, thanks to the present methods.

In addition, the present approach is well suited for monitoring S25-S30 a temporal evolution of focused signals. This is achieved by repeatedly receiving datasets, i.e., by receiving S25 time series of datasets, each pertaining to respective detector pair coordinates $(\theta_d, p_d)$. Thus, time series of supersets are formed, where each superset comprises several tomographic datasets and each dataset is associated with respective detector pair coordinates $(\theta_d, p_d)$. Then, for each selected point y, the received datasets are coherently combined S27, following the same approach as discussed above, by weighting the datasets according to relevant beamforming weights $w^*(y)=\omega(\theta_d, p_d; y)$, so as to obtain time series of signals focusing on the selected point(s) y. The signals can subsequently be displayed S30.

Assuming a fixed detection configuration, monitoring can be achieved by repeatedly performing steps S25, S27, S28, and S30. An interactive monitoring can be achieved by repeatedly performing, on the one hand, steps S25, S27, S28, S30 and, on the one hand, steps S22, S23, S26. The multiple time series monitored may for example describe the evolution of a metabolic activity across time for specific points of interest in the organ.

Now, the monitoring may include specific computational steps S28, which, in addition to the mere computation and monitoring of the reconstructed signals, may involve functions derived from the reconstructed signals, such as gradients. For example, gradients may be monitored, such that additional data may come to be displayed (such as visual cues), in addition to intensities of the reconstructed signals, e.g., when a substantial change is detected during the monitoring.

Next, according to a final aspect, the invention can be embodied as a computer program product for beamforming datasets from a tomographic detection system. This computer program product comprises a computer readable storage medium having program instructions embodied therewith, wherein the program instructions are executable by one or more processors, to cause to take steps according to the present methods. Aspects of this computer program products are discussed in detail in sect. 3. This program may for instance be run at a computerized device 20 in data communication with the detection unit 10 and the display unit 30 or remotely, at a server. Many other architectures can be contemplated, as the person skilled in the art will appreciate.

The above embodiments have been succinctly described in reference to the accompanying drawings and may accommodate a number of variants. Several combinations of the above features may be contemplated, as discussed below in sect. 2.

2. Specific Embodiments

This section describes embodiments that are more specifically directed to positron emission tomography (PET). They relate to imaging and sensing with PET scanners. This section further presents a mathematical justification of concepts used in this invention. It notably describes how beamforming techniques and consequently imaging by beamforming can be performed in the context of PET.

The beamforming weights are assumed to be sampled from an analytically-specified beamforming function. Since the weights are data-independent, the resulting imaging algorithm is extremely efficient. Accordingly, embodiments as described below allow an efficient production of PET images, together with higher resolution and contrast, compared to known methods, as demonstrated by simulations. Such embodiments further make it possible to monitor a specific region of an organ under study without imaging the whole organ, which is currently not possible according to the methods known so far, to the knowledge of the present inventors. Applications to medical imaging technology can thus greatly benefit from such embodiments.

Beamforming techniques have perhaps never been applied to PET data so far. Traditional imaging methods mostly rely on the so-called filtered back projection algorithm or other statistical methods, which do not leverage beamforming at all. On the contrary, embodiments as discussed herein rely on a notional continuous detector ring, and derive a beamforming function associated to a Dirac-like beamshape. Thus, the beamforming function can be sampled for specific coordinates of the detectors composing the scanner, to form an empirical beamshape.

Application of the methods discussed herein are aimed at beamforming PET data, e.g., so as to estimate an organ's metabolic activity at various location, or at specific locations. I.e., even though novel beamforming techniques discussed herein make it possible to focus on specific locations (e.g., of an organ under investigation), 2D imaging can nevertheless be obtained by scanning over an imaging domain. That is, images can be formed by scanning over grids of points and the scanning can be performed in parallel on each grid point, hence yielding a very efficient algorithm. The beamforming weights are sampled at the locations of the scintillation detectors from a continuous beamforming function associated to a continuous detector ring and independent from the data. The beamforming function being analytically specified, the overall processing pipeline is numerically stable.

This process can be summarized as follows:
The following inputs are used:
A prescribed detector ring composed of D detector pairs;
Data recorded by the detectors through time;
A grid or set of physical points on which to evaluate the organ's metabolic activity; and
A bandwidth and window type for the computation of the ramp filter.
Given a grid point, as well as a choice of bandwidth and window, the beamforming weights are computed from a beamforming function analytically specified. The array empirical beamshape can be steered towards various points to scan the region of interest.

The beamforming weights obtained are applied to the data collected, yielding the metabolic activity for the scanned grid points.

The output is either an image (intensities associated to each grid point scanned) and/or multiple time series describing the evolution of the metabolic activity across times for specific points of interest in the organ.

2.1. Implementations

2.1.1 Imaging by Beamforming

Let $n=[n(\theta_1, p_1), \ldots, n(\theta_D, p_D)] \in \mathbb{R}^D$ be the data recorded by the PET scanner. One can form an estimate $\hat{\lambda}$ of the metabolic process of interest (e.g., an image of an organ) over a domain $\mathcal{B} \subset \mathbb{R}^2$ as $$\hat{\lambda}(y) = w(y)^T n = \sum_{d=1}^{D} w_d(y) n(\theta_d, p_d), \forall y \in \mathcal{B} \subset \mathbb{R}^2, \quad (1)$$

where $w(y) \in \mathbb{R}^D$ is the beamforming vector for the steering position $y \in \mathcal{B}$. This image is the result of scanning the imaging domain $\mathcal{B}$ with the array beamshape $$b(x) = \sum_{d=1}^{D} w_d(y) \delta(p_d - \langle x, \xi_{\theta_d} \rangle), \forall x \in \mathbb{R}^2 \quad (2)$$

for various steering points $y$ covering $\mathcal{B}$.

Figure 1:
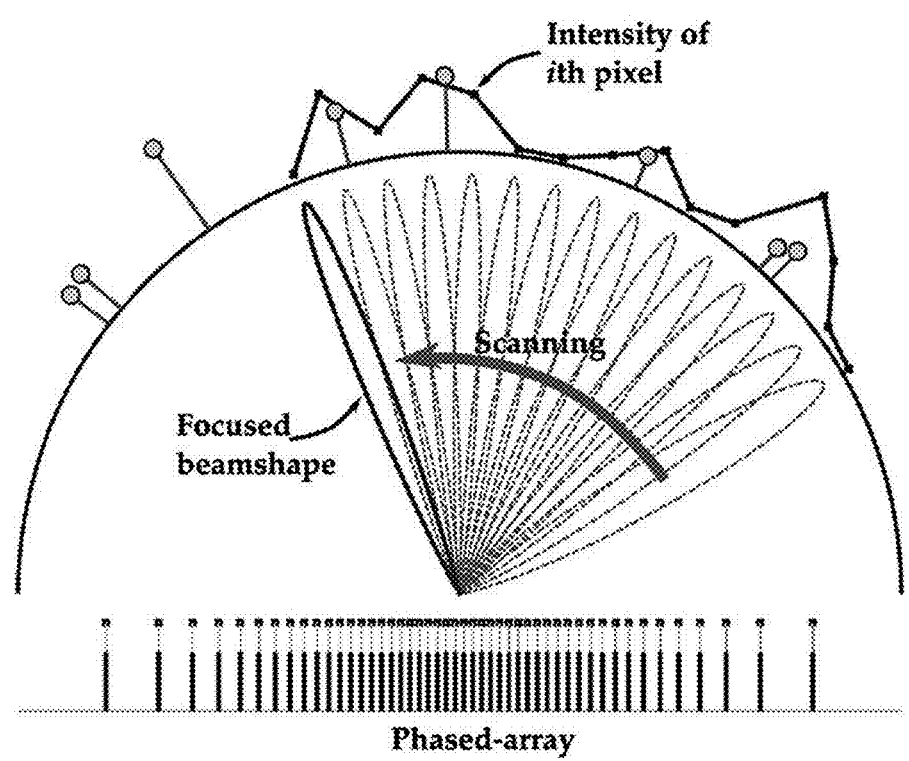
FIG. 1 schematically illustrates spatial aspects of a beamforming process for a phased array of detectors in one embodiment, as perceived by the present inventors. Phased array detection systems and corresponding beamforming processes are otherwise known per se.
Figure 2A:
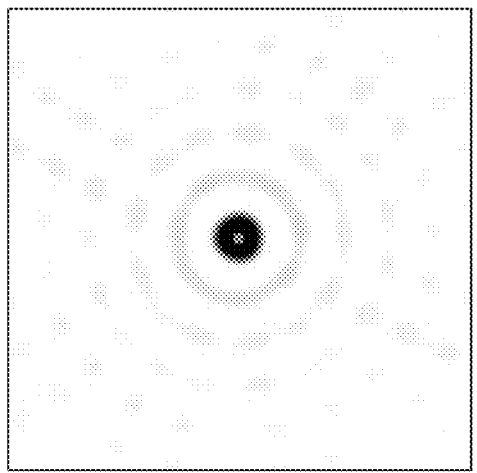
FIGS. 2A and 2B show density plots of empirical point-spread-functions (PSFs), illustrating the response of two imaging systems to a single point source in one embodiment.
Figure 2B:
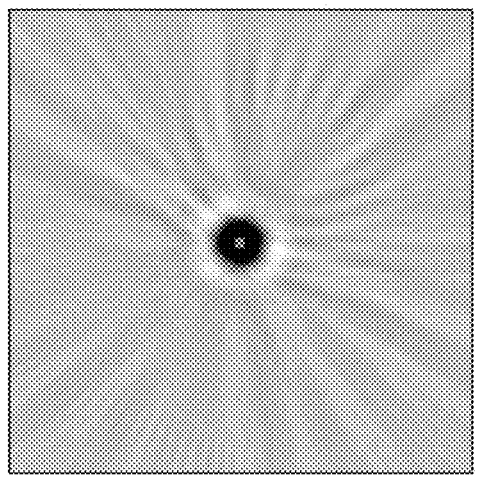
Figure 2C:
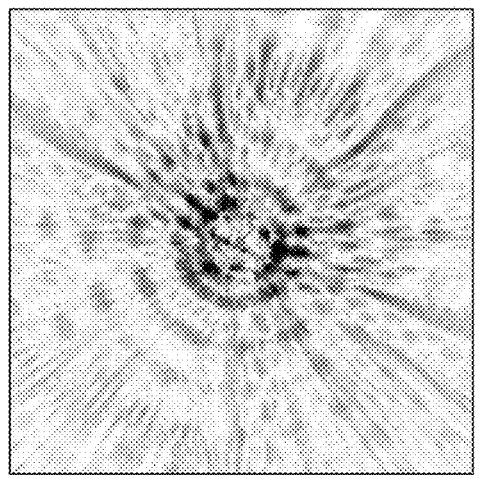
FIG. 2C shows the difference between the two PSFs.

This beamshape is deterministic, data-independent, and depends only on the geometry of the detector ring. Note that the function b depends both on x and y but y is rather regarded as a parameter of the function, whence the notation b(x). As defined above, this array beamshape can also be regarded as a point-spread function (PSF) of the proposed imager, i.e., the response of the tool to a point source, inasmuch as b(x) fully characterizes the output image as well as its quality. In that respect, it is worth noting that embodiments as discussed herein specifically impact the PSF of the imager, as illustrated in FIGS. 2A-2C.

The beamforming weights $w_d(y)$, $d=1, \ldots, D$ in eq. (1) can be sampled from a variety of beamforming function, as discussed below.

Rectangular Window: In this case, the Ramp filter h is truncated with a rectangular window. The rectangular Ramp filter is defined in the Fourier domain by $\hat{h}_{rec}(f) := |f| \chi(f \leq f_0)$, for some $f_0 > 0$. With this choice of regularization, the beamforming function is given by (see sect. 2.2.3 for a mathematical justification):

$$\omega_{rec}(\theta, p; y) = \begin{cases} \frac{f_0^2}{2} & \text{if } p = \langle y, \xi_\theta \rangle, \\ \frac{f_0 \sin[2\pi f_0(p - \langle y, \xi_\theta \rangle)]}{\pi(p - \langle y, \xi_\theta \rangle)} + \\ \frac{\cos[2\pi f_0(p - \langle y, \xi_\theta \rangle)] - 1}{2\pi^2(p - \langle y, \xi_\theta \rangle)^2} & \text{otherwise.} \end{cases} \quad (3)$$

Figure 3A:
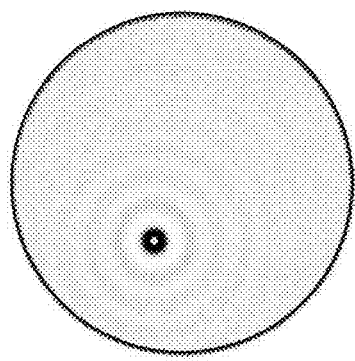
FIGS. 3A-3F compare rectangular and triangular ramp filters used to derive beamforming functions, from which beamforming weights can be obtained, as in embodiments. In detail.
Figure 3B:
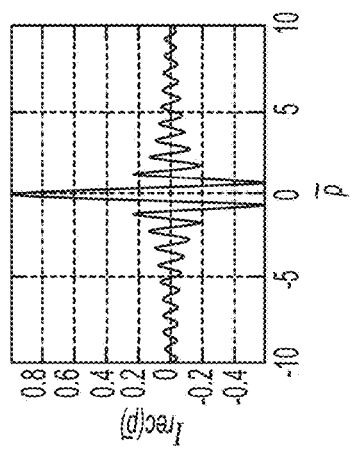
Figure 3C:
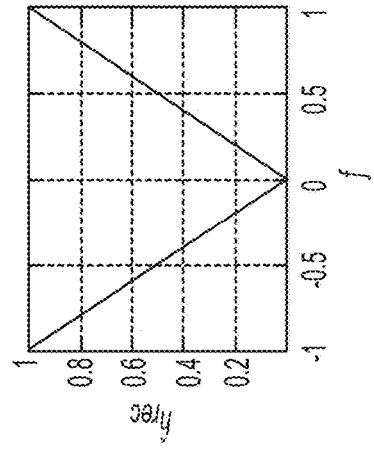

The beamforming weights are hence given by $w_d(y) = \omega_{rec}(\theta_d, p_d; y)$. This results in the estimate:

$$\hat{\lambda}_{rec}(y) = \sum_{d=1}^{D} \mathcal{I}_{rec}(p_d - \langle y, \xi_{\theta_d} \rangle) n(\theta_d, p_d), \forall y \in \mathcal{B} \subset \mathbb{R}^2 \quad (4)$$

where $\mathcal{I}_{rec}$ is defined in eq. (16) below. FIGS. 3A-3C show depictions of corresponding rectangular Ramp filter function $\hat{h}_{rec}$, the function $\mathcal{I}_{rec}$ and the array beamshape.

Triangular Window: In this case, we truncate the Ramp filter h with a triangular window. The triangular Ramp filter is defined in the Fourier domain by $$\hat{h}_{tri}(f) := |f| \left(1 - \frac{|f|}{f_0}\right) \chi(f \leq f_0),$$

for some $f_0 > 0$. With this choice of regularization, the beamforming function is given by (see sect. 2.2.4 for a mathematical justification):

$$\omega_{tri}(\theta, p; y) = \begin{cases} \frac{f_0^2}{3} & \text{if } p = \langle y, \xi_\theta \rangle, \\ -\frac{\cos^2[\pi f_0(p - \langle y, \xi_\theta \rangle)]}{\pi^2(p - \langle y, \xi_\theta \rangle)^2} + \\ \frac{\sin[2\pi f_0(p - \langle y, \xi_\theta \rangle)]}{2\pi^3 f_0(p - \langle y, \xi_\theta \rangle)^3} & \text{otherwise.} \end{cases} \quad (5)$$

Figure 3D:
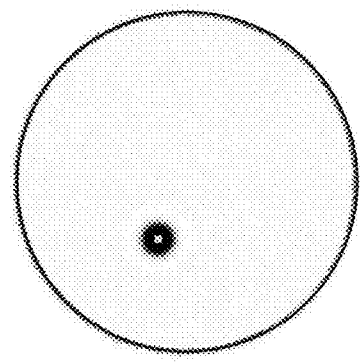
Figure 3E:
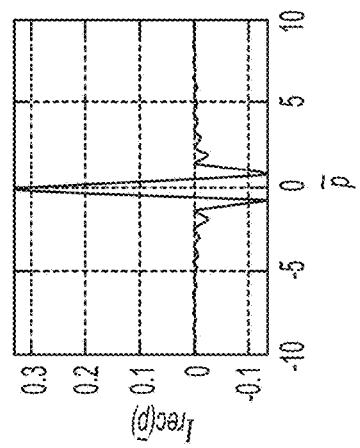
Figure 3F:
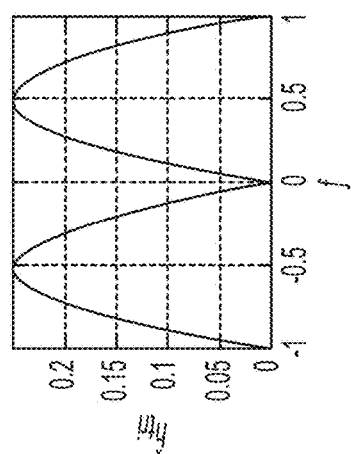

The beamforming weights are hence given by $w_d(y) = \omega_{tri}(\theta_d, p_d; y)$. This results in the estimate:

$$\hat{\lambda}_{tri}(y) = \sum_{d=1}^{D} \mathcal{I}_{tri}(p_d - \langle y, \xi_{\theta_d} \rangle) n(\theta_d, p_d), \forall y \in \mathcal{B} \subset \mathbb{R}^2 \quad (6)$$

where $\mathcal{I}_{tri}$ is defined in eq. (21). Examples of a triangular Ramp filter function $\hat{h}_{tri}$, a function $\mathcal{I}_{tri}$ and a corresponding array beamshape are depicted in FIGS. 3D to 3F.

Images obtained with both types (rectangular, triangular) of windows are shown in FIGS. 4A-4I and FIGS. 5A-5L, where a comparison is further made with results as obtained from a known filtered back projection algorithm. It can be seen that the rectangular window produces sharper images but with more artifacts than the triangular window for a same window size $f_0$ (e.g., in $m^{-1}$). It is, however, possible to achieve higher resolutions with the triangular window by increasing its window size $f_0$ until the main lobe of the array beamshape becomes as narrow as with the rectangular window (see FIGS. 5G-5I). Finally, one observes that unlike images obtained with the invention, the filtered back projection images shown in the last rows of FIGS. 4A-4I and FIGS. 5A-5L have non uniform errors, with a higher sensitivity in the center than at the edges.

Welch Window: Similarly, one may define a Welch-type window, as in the Welch's method used for estimating the power of a signal at different frequencies in spectral density estimations. Namely, one may define:

$$\omega_{wel}(\theta, p; y) = \frac{h_{wel}(p - \langle y, \xi_\theta \rangle)}{4\pi^2}, \forall (\theta, p) \in [0, \pi[ \times \mathbb{R},$$

leading to $$h_{wel}(p) = \begin{cases} \frac{f_0^2}{2} & \text{if } p = 0, \\ -\frac{2\cos(2\pi f_0 p) + 1}{2\pi^2 p^2} + \frac{3\sin(2\pi f_0 p)}{2f_0\pi^3 p^3} + \\ \quad \ldots + \frac{3(\cos(2\pi f_0 p) - 1)}{4\pi^4 f_0^2 p^4} & \text{otherwise.} \end{cases}$$

2.1.2. Single Point Focusing and Monitoring

Assume that the analyst is only interested in the metabolic activity of specific points $\{y_1, \ldots, y_N\} \subset \mathcal{B}$ of an organ. Then, embodiments of the present invention can be used to beamform towards those specific points and monitor their activity through time, yielding a multidimensional time series:

$$\lambda(t) = \begin{bmatrix} \hat{\lambda}(y_1, t) \\ \vdots \\ \hat{\lambda}(y_N, t) \end{bmatrix} = \begin{bmatrix} w(y_1)^T \\ \vdots \\ w(y_N)^T \end{bmatrix} n(t).$$

2.2 Technical Background

This section describes the background information from a mathematical point of view, and justifies the invention method.

2.2.1 The Physics of PET

For example, as primary source of the brain's energy, glucose will concentrate in various regions of the brain in quantities proportional to the brain's metabolic activity. Then, by labeling glucose with a radioactive substance (as schematically illustrated in FIG. 6A, step S1), the subsequent positron emissions will also be directly proportional to glucose consumption and therefore to the brain's metabolic activity. Thus, if one is able to record the locations of each emission, one can produce a portrait of the brain's metabolic activity.

Unfortunately, one cannot identify the exact location of positron emissions. However, one can determine a cylindrical volume in which the emission occurred. In fact, when a positron is emitted, it quickly annihilates with an electron naturally present in the brain's medium. This annihilation generates two gamma rays, flying off in nearly opposite random directions, as depicted in FIG. 6A. Therefore, by positioning a ring of scintillation detectors around the head of the patient 2, one can detect those gamma rays, which hit in coincidence a pair of detectors (see FIG. 6A or 6B).

A detector pair defines a cylindrical volume (also called detector tube), which gives partial information as to the location of the positron emission. During a PET acquisition, the scanner will record each coincidence and count the total number of coincidences for each detector tube. For an ideal detector tube, infinitely thin (hence coinciding with the so-called line-of-response, or LOR), the expected number of coincidences $n(\theta_d, p_d)$ recorded is given by $$\mathbb{E}[n(\theta_d,p_d)] = \int_{\mathbb{R}^2} \lambda(x)\delta(p_d - \langle x, \xi_{\theta_d} \rangle) dx,$$

where $\lambda(x)$ is the metabolic activity one wishes to recover and $(\theta_d, p_d)$ are the polar coordinates of the detector tube for pair d.

In other words, a decaying radio-isotope emits a positron that travels a short distance before annihilating with an electron. Such an annihilation produces two high-energy photons propagating in nearly opposite directions. Thus, if two photons are detected within a short timing window (the coincidence timing window), an event, i.e., a true coincidence, is recorded along the line (i.e., the LOR) connecting the two detectors, specified by $(\theta_d, p_d)$, where $\theta_d$ and $p_d$ respectively corresponds to the angle of orientation of the LOR of pair d and the distance of this LOR from the center of the scan field.

For example, FIGS. 4A-4I assumes D=31125 detector pairs (or detector tubes, or LOR). I.e., if L is the number of scintillation detectors, the number of unique pairs is given by D=L(L−1)/2, meaning that L=250 detectors are assumed to be involved in this case.

Figure 7B:
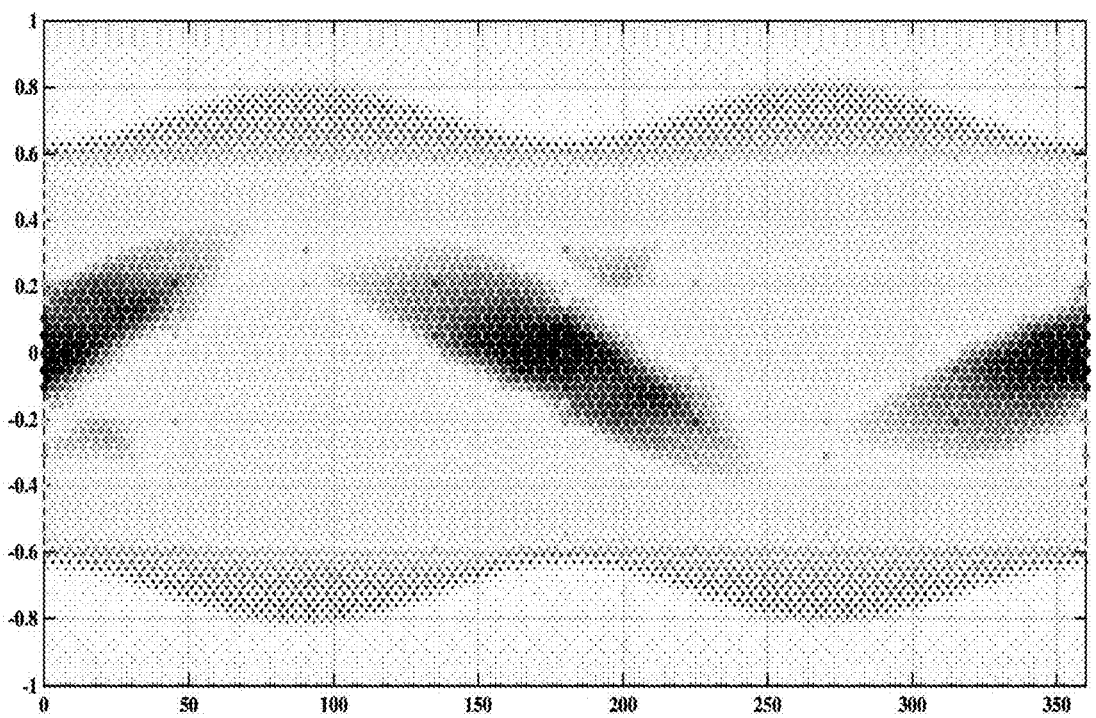

In practice, the observed data is perturbed with Poisson-like noise, fluctuating around the mean. It is customary to display PET data in the form of a sinogram such as depicted in FIGS. 7A-7B.

2.2.2 Mathematical Considerations Underlying Embodiments of the Invention

The aim is to coherently combine S26 signals, so as to achieve desired radiation patterns. Mathematically speaking, this translates into a linear combination of the data, which in turn spatially filters the observed signal with the array beamshape. As it may be realized, one may, by analogy with usual beamforming, define beamformed data in the context of PET as:

$$\mu = w^T n = \sum_{d=1}^{D} w_d n(\theta_d, p_d), \qquad (7)$$

where $n(\theta_d, p_d)$ is the number of gamma ray coincidences recorded by the detector pair d with coordinates $(\theta_d, p_d) \in [0, \pi] \times \mathbb{R}$. As mentioned earlier, the signal follows a Poisson distribution with mean:

$$\mathbb{E}[n(\theta_d,p_d)] = \int_{\mathbb{R}^2} \lambda(x)\delta(p_d - \langle x, \xi_{\theta_d} \rangle) dx, \qquad (8)$$

where $\xi_{\theta_d} = [\cos(\theta_d), \sin(\theta_d)] \in \mathbb{R}^2$ and $\lambda: \mathbb{R}^2 \to \mathbb{R}_+$ is the intensity function, proportional to the signal (metabolic activity) one wishes to recover.

Plugging Eq. (8) into Eq. (7) yields on expectation $$\mathbb{E}[\mu] = \int_{\mathbb{R}^2} \lambda(x) \left[ \sum_{d=1}^{D} w_d \delta(p_d - \langle x, \xi_{\theta_d} \rangle) \right] dx = \langle \lambda, b \rangle.$$

Hence, beamforming the data equivalently filters the intensity function $\lambda$ with the beamshape $$b(x) := \sum_{d=1}^{D} w_d \delta(p_d - \langle x, \xi_{\theta_d} \rangle). \qquad (9)$$

Assuming one could choose beamforming weights $\{w(y)\}_d$ such that $b(x) \simeq \delta(x-y)$ for some $y \in \mathbb{R}^2$, then the reproducing property of the Dirac delta function would allow us to form the following estimate of λ:

$$\hat{\lambda}(y) = \hat{\mu}(y) = w(y)^T n, \forall y \in \mathbb{R}^2.$$

This imaging procedure bears some resemblance with a classic beamforming procedure (or B-scan) as used in classical phased-array signal processing, except that beamforming weights need here be computed according to the geometry of each detector and the points of interest y. In addition, no delay need be introduced here. Also, the geometry is somehow inverted, compared to phased array where beamforming is classically used. I.e., the scanned objects here reside within the plane or volume enclosed by the detectors, whereas objects sensed in phased arrays are normally outside (and far from the) surface or volume enclosed by the detectors. Despites, such differences, beamforming can be adapted to the context of tomographic scanners, as demonstrated herein.

Indeed, it is possible to design a Dirac-like beamshape, also in this context. To that aim, one first introduces a notional continuous detector field on $[0, \pi] \times \mathbb{R}$, and derive a beamforming function associated to the Dirac beamshape. This approach, incidentally, can be generalized to 3D detector configurations, involving several contiguous rings of detectors. Then, we sample the beamforming function for the specific detector pair locations and form the empirical beamshape. For a continuous detector ring, the beamshape is given by $$b(x) = \int_0^\pi \int_\mathbb{R} \omega(\theta, p) \delta(p - \langle x, \xi_\theta \rangle) dp\, d\theta = \int_0^\pi \omega(\theta, \langle x, \xi_\theta \rangle) d\theta, \quad (10)$$

where $\omega: [0, \pi] \times \mathbb{R} \to \mathbb{R}$ can be regarded as a beamforming function, adapted to the particular context of PET.

From the inversion formula of the 2D Radon transform, one can formulate $$\delta(x - y) = \int_o^\pi [h * \mathcal{R}\{\delta(x-y)\}(\theta, \cdot)](\langle x, \xi_\theta \rangle)\, d\theta, \quad (11)$$

with $h: \mathbb{R} \to \mathbb{R}$ being the Ramp filter defined in the Fourier domain as $\hat{h}(f) = |f|$. Hence, choosing the beamforming function ω in (10) as $$w(\theta, p) = [h * \mathcal{R}\{\delta(x-y)\}(\theta, \cdot)](p) \quad (12)$$

yields the desired beamshape $b(x) = \delta(x-y)$.

In practice, since the data is noisy and to avoid numerical instabilities, a windowed Ramp filter can be used. We may notably use two window types: rectangular and triangular. With such windows, eq. (12) admits a convenient close form solution, which makes it possible to compute the beamforming weights to be applied to the data. The derivation of the beamforming function in both cases are discussed in the subsequent sections.

For a given scanner, beamforming weights $w_d$ as used in eq. (9) can be computed by sampling the beamforming function for a finite number D of detector pairs with coordinates $(\theta_d, p_d)$, hence yielding an empirical beamshape approximating (11), see FIGS. 8A-8B. The main lobe of the achieved beamshape gets narrower as the number of detectors D increases and the sidelobes become more and more wiggly as $f_0$ increases.

2.2.3 Derivation of the Beamforming Function for the Rectangular Window

Assume that the Ramp filter h is truncated with a rectangular window, defined in the Fourier domain by $\hat{h}_{rec}(f) := |f| \chi(f \leq f_0)$, for some $f_0 > 0$. Then, the beamforming function ω in Eq. (12) becomes:

$$\begin{aligned}
\omega_{rec}(\theta, p; y) &= [h_{rec} * \mathcal{R}\{\delta(x-y)\}(\theta, \cdot)](p) \quad (13)\\
&= [h_{rec} * \delta(p - \langle y, \xi_\theta \rangle)](p)\\
&= \mathcal{F}^{-1}\{\hat{h}_{rec}(f) \times e^{-j2\pi f \langle y, \xi_\theta \rangle}\}(p)\\
&= \int_\mathbb{R} |f| \chi(f \leq f_0) e^{-j2\pi f \langle y, \xi_\theta \rangle} e^{j2\pi f p} df\\
&= \int_\mathbb{R} |f| \chi(f \leq f_0) e^{j2\pi f \tilde{p}} df, \text{ where } \tilde{p} = p - \langle y, \xi_\theta \rangle,\\
&= \int_{-f_0}^{f_0} |f| e^{j2\pi f \tilde{p}} df\\
&= 2\int_0^{f_0} f \cos(2\pi f \tilde{p}) df := \mathcal{I}_{rec}(\tilde{p}).
\end{aligned}$$

Splitting the computation in two parts: $\tilde{p}=0$ and $\tilde{p} \neq 0$. For $\tilde{p}=0$ we have $$\mathcal{I}_{rec}(\tilde{p}) = 2\int_0^{f_0} f\, df = [f^2]_0^{f_0} = f_0^2, \text{ for } \tilde{p} = 0. \quad (14)$$

For $\tilde{p} \neq 0$ integration by parts yields $$\begin{aligned}
\mathcal{I}_{rec}(\tilde{p}) &= \left[f \frac{\sin(2\pi f \tilde{p})}{\pi \tilde{p}}\right]_0^{f_0} - \frac{1}{\pi \tilde{p}} \int_0^{f_0} \sin(2\pi f \tilde{p}) df \quad (15)\\
&= \left[f \frac{\sin(2\pi f \tilde{p})}{\pi \tilde{p}}\right]_0^{f_0} + \frac{1}{\pi \tilde{p}} \left[\frac{\cos(2\pi f \tilde{p})}{2\pi \tilde{p}}\right]_0^{f_0}\\
&= f_0 \frac{\sin(2\pi f_0 \tilde{p})}{\pi \tilde{p}} + \frac{1}{2\pi^2 \tilde{p}^2}(\cos(2\pi f_0 \tilde{p}) - 1), \quad \forall \tilde{p} \neq 0.
\end{aligned}$$

Combining (14) and (15) leads to $$\mathcal{I}_{rec}(\tilde{p}) = \begin{cases} f_0^2 & \text{if } \tilde{p} = 0, \\ \frac{f_0 \sin(2\pi f_0 \tilde{p})}{\pi \tilde{p}} + \frac{\cos(2\pi f_0 \tilde{p}) - 1}{2\pi^2 \tilde{p}^2} & \text{otherwise,} \end{cases} \quad (16)$$

and hence from (13) the beamforming function is obtained as $$\omega_{rec}(\theta, p; y) = \begin{cases} f_0^2 & \text{if } p = \langle y, \xi_\theta \rangle, \\ \frac{f_0 \sin[2\pi f_0(p - \langle y, \xi_\theta \rangle)]}{\pi (p - \langle y, \xi_\theta \rangle)} + \\ \frac{\cos[2\pi f_0(p - \langle y, \xi_\theta \rangle)] - 1}{2\pi^2 (p - \langle y, \xi_\theta \rangle)^2} & \text{otherwise.} \end{cases} \quad (17)$$

Using Taylor expansions of the cosine and sine, it is possible to show that $\mathcal{I}_{rec}$ and hence the beamforming function $\omega_{rec}$ in (17) are continuous about $\tilde{p}=0$.

2.2.4 Derivation of the Beamforming Function for the Triangular Window

Assume that we truncate the Ramp filter h with a triangular window, defined in the Fourier domain by $$\tilde{h}_{tri}(f) := |f|\left(1 - \frac{|f|}{f_0}\right)\chi(f \le f_0),$$

for some $f_0 > 0$. Then, similarly to the case with the rectangular window, the beamforming function $\omega$ in (12) can be written as:

$$\omega_{tri}(\theta, p; y) = \int_R |f|\left(1 - \frac{|f|}{f_0}\right)\chi(f \le f_0)e^{j2\pi f \tilde{p}}df, \quad (18)$$

where $\tilde{p} = p - \langle y, \xi_\theta \rangle$, $$= 2\int_0^{f_0} f\left(1 - \frac{f}{f_0}\right)\cos(2\pi f \tilde{p})df := \mathcal{I}_{tri}(\tilde{p}).$$

Again, splitting the computation in two cases, $\tilde{p}=0$ and $\tilde{p} \ne 0$, we get, for $\tilde{p}=0$:

$$\mathcal{I}_{tri}(\tilde{p}) = 2\int_0^{f_0} f\left(1 - \frac{f}{f_0}\right)df = \left[f^2 - \frac{2f^3}{3f_0}\right]_0^{f_0} = \frac{f_0^2}{3}, \quad (19)$$

for $\tilde{p} = 0$.

For $\tilde{p} \ne 0$ we use integration by parts repeatedly and obtain $$\mathcal{I}_{tri}(\tilde{p}) = 2\int_0^{f_0} f\cos(2\pi f \tilde{p})df - 2\int_0^{f_0} \frac{f^2}{f_0}\cos(2\pi f \tilde{p})df \quad (20)$$

$$= \mathcal{I}_{rec}(\tilde{p}) - \left[\frac{f^2}{f_0}\frac{\sin(2\pi f \tilde{p})}{\pi \tilde{p}}\right]_0^{f_0} + \frac{2}{f_0 \pi \tilde{p}}\int_0^{f_0} f\sin(2\pi f \tilde{p})df$$

$$= \mathcal{I}_{rec}(\tilde{p}) - \left[\frac{f^2}{f_0}\frac{\sin(2\pi f \tilde{p})}{\pi \tilde{p}}\right]_0^{f_0} - \frac{1}{f_0 \pi \tilde{p}}\left[f\frac{\cos(2\pi f \tilde{p})}{\pi \tilde{p}}\right]_0^{f_0} +$$

$$\frac{1}{f_0 \pi^2 \tilde{p}^2}\int_0^{f_0}\cos(2\pi f \tilde{p})df$$

$$= \mathcal{I}_{rec}(\tilde{p}) - \left[\frac{f^2}{f_0}\frac{\sin(2\pi f \tilde{p})}{\pi \tilde{p}}\right]_0^{f_0} - \frac{1}{f_0 \pi \tilde{p}}\left[f\frac{\cos(2\pi f \tilde{p})}{\pi \tilde{p}}\right]_0^{f_0} +$$

$$\frac{1}{f_0 \pi^2 \tilde{p}^2}\left[\frac{\sin(2\pi f \tilde{p})}{2\pi \tilde{p}}\right]_0^{f_0}$$

$$= \mathcal{I}_{rec}(\tilde{p}) - \frac{f_0 \sin(2\pi f_0 \tilde{p})}{\pi \tilde{p}} - \frac{\cos(2\pi f_0 \tilde{p})}{\pi^2 \tilde{p}^2} + \frac{\sin(2\pi f_0 \tilde{p})}{2\pi^3 f_0 \tilde{p}^3}$$

Combining (15), (19) and (20) yields, after simplifications $$\mathcal{I}_{tri}(\tilde{p}) = \begin{cases} \frac{f_0^2}{3} & \text{if } \tilde{p} = 0, \\ -\frac{\cos^2(\pi f_0 \tilde{p})}{\pi^2 \tilde{p}^2} + \frac{\sin(2\pi f_0 \tilde{p})}{2\pi^3 f_0 \tilde{p}^3} & \text{otherwise.} \end{cases} \quad (21)$$

Hence, from Eq. (18), one may write the beamforming function as $$\omega_{tri}(\theta, p; y) = \begin{cases} \frac{f_0^2}{3} & \text{if } p = \langle y, \xi_\theta \rangle, \\ -\frac{\cos^2[\pi f_0(p - \langle y, \xi_\theta \rangle)]}{\pi^2 (p - \langle y, \xi_\theta \rangle)^2} + & \\ \frac{\sin[2\pi f_0(p - \langle y, \xi_\theta \rangle)]}{2\pi^3 f_0(p - \langle y, \xi_\theta \rangle)^3} & \text{otherwise.} \end{cases} \quad (22)$$

Using Taylor expansions of the cosine and sine functions, it is possible to show that $\mathcal{I}_{tri}$ and hence the beamforming function $\omega_{tri}$ in Eq. (22) are continuous about $\tilde{p}=0$.

2.2.5 Other Types of Windows

Other types of windows can similarly be derived, such as a Welsh-type window, as evoked earlier, for which the derivation of the beamforming function is straightforward. In other variants, Gaussian windows may be devised, for example.

2.3 Final Considerations

The above considerations extend to contexts where moving detectors are used. Yet, instead of being associated with particular detectors pairs, the datasets processed are associated to specific detection geometries. The mathematical considerations and resulting analytical functions remain, however, essentially unchanged.

3. Systems, Methods and Computer Program Products

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the C programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated.

What is claimed is:

1. A method of beamforming datasets from a tomographic detection system comprising scintillation detectors arranged in D detector pairs, $D \geq 1$, the detectors adapted to count radiation hits, the method comprising:

receiving a tomographic dataset, for each detector pair coordinates $(\theta_d, p_d)$ of a detector pair d of the D detector pairs, so as to obtain a plurality of tomographic datasets, each associated with respective detector pair coordinates $(\theta_d, p_d)$; and for each point y of interest, coherently combining the received datasets by weighting the datasets according to respective beamforming weights $w_d(y) = \omega(\theta_d, p_d; y)$, based on said respective detector pair coordinates $(\theta_d, p_d)$ and coordinates of said each point y of interest, so as to obtain a signal focusing on said each point y.

2. The method according to claim 1, further comprising, prior to coherently combining the received datasets:
computing the beamforming weights by sampling a beamforming function $\omega(\theta, p; y)$ according to said respective detector pair coordinates $(\theta_d, p_d)$ and said coordinates of said each point y of interest.

3. The method according to claim 2, wherein
each of the computed beamforming weights is independent from the tomographic datasets obtained.

4. The method according to claim 3, wherein
the beamforming weights are computed in parallel on a plurality of points of interest.

5. The method according to claim 2, wherein
the beamforming function is computable as a function of
a reduced distance $\tilde{p}=p-\langle y, \xi_\theta \rangle$ between a radial coordinate p of detector pair coordinates $(\theta, p)$ and a projection $\langle y, \xi_\theta \rangle$ of said each point y of interest on a radial direction, wherein said detector pair coordinates $(\theta, p)$ involve an angle $\theta$ of orientation of a line defined by a detector pair and a minimal distance p of this line from a center of a scan field of the detectors, the minimal distance measured along said radial direction, the latter defined by a vector $\xi_\theta$, which is normal to said line, in a polar coordinate system.

6. The method according to claim 5, wherein
the beamforming function is analytically defined for each value of the reduced distance.

7. The method according to claim 6, wherein
the beamforming function is defined so as to be continuous at $\tilde{p}=p-(y, \xi_\theta)=0$.

8. The method according to claim 2, wherein
the beamforming function is derived from a windowed version of a ramp filter function $\hat{h}(f)$ of the tomographic detection system, which ramp filter function corresponds to a Dirac delta function.

9. The method according to claim 8, wherein
the beamforming function is computable as a function of the reduced distance $\tilde{p}$, which is the conjugate variable of the argument f of said ramp filter function $\hat{h}(f)$.

10. The method according to claim 9, wherein
the beamforming function used is derived from a band-limited ramp filter function $\hat{h}(f)$: $=|f|\chi(f \leq f_0)$, $f_0 > 0$, of the tomographic detection system, wherein the function $\hat{h}(f)$ is truncated, in the Fourier domain, with a window function $\chi(f \leq f_0)$, according to a window size $f_0$ of the detection system, and wherein the beamforming function is representable as a back Fourier transform of the truncated ramp filter function.

11. The method according to claim 10, wherein
said window function is one of:
a rectangular window function;
a triangular window function; and
a Welch window function.

12. The method according to claim 1, wherein
the tomographic detection system is one of:
a positron emission tomography detection system;
an X-ray computed tomography scan system; and
an ultrasound tomography detection system.

13. The method according to claim 1, wherein
the tomographic detection system comprises D detector pairs, $D \geq 2$, each of the pairs having fixed detector pair coordinates $(\theta_d, p_d)$, and
each of the tomographic datasets received correspond to respective, fixed detector pair coordinates $(\theta_d, p_d)$ of a respective detector pair d of the D detector pairs.

14. The method according to claim 13, wherein
the detectors have a ring arrangement.

15. The method according to claim 13, wherein the method further comprises, prior to coherently combining the received datasets:
computing the beamforming weights $w_d(y)=\omega(\theta_d, p_d; y)$ by sampling a beamforming function $\omega(\theta, p; y)$ according to the fixed detector pair coordinates $(\theta_d, p_d)$ respectively corresponding to the received datasets and the coordinates of said each point y of interest.

16. The method according to claim 1, further comprising
receiving a selection of a subset of one or more points of interest out of a defined set of points, whereby the received datasets are coherently combined for each point of the subset of points of interest.

17. The method according to claim 16, further comprising
monitoring a temporal evolution of signals focused on said each point of the selected subset of points of interest, wherein monitoring comprises:
receiving time series of tomographic datasets, for said each detector pair coordinates $(\theta_d, p_d)$, so as to obtain time series of supersets, each of the supersets comprising a plurality of tomographic datasets, wherein each of the datasets is associated with respective detector pair coordinates $(\theta_d, p_d)$; and
for each point y of the selected subset of points of interest, coherently combining the received datasets by weighting the datasets according to respective beamforming weights $w_d(y)=\omega(\theta_d, p_d; y)$, based on respective detector pair coordinates $(\theta_d, p_d)$ and coordinates of said each point y, so as to obtain time series of signals focusing on said each point y.

18. The method according to claim 1, further comprising
displaying the monitored temporal evolution of signals.

19. A tomographic detection system, comprising
scintillation detectors arranged in D detector pairs, $D \geq 1$, the detectors adapted to count radiation hits; and
a reconstruction module, in data communication with the detectors, the module configured for:
receiving a tomographic dataset, for each detector pair coordinates $(\theta_d, p_d)$ of a detector pair d of the D detector pairs, so as to obtain a plurality of tomographic datasets, each associated with respective detector pair coordinates $(\theta_d, p_d)$; and
for each point y of interest, coherently combining the received datasets by weighting the datasets according to respective beamforming weights $w_d(y)=\omega(\theta_d, p_d; y)$, based on said respective detector pair coordinates $(\theta_d, p_d)$ and coordinates of said each point y of interest, so as to obtain a signal focusing on said each point y.

20. A computer program product for beamforming datasets from a tomographic detection system that comprises scintillation detectors arranged in D detector pairs, $D \geq 1$, where the detectors are adapted to count radiation hits, the computer program product comprising a computer readable storage medium having program instructions embodied therewith, the program instructions executable by one or more processors, to cause to
receive a tomographic dataset, for each detector pair coordinates $(\theta_d, p_d)$ of a detector pair d of the D detector pairs, so as to obtain a plurality of tomographic datasets, each associated with respective detector pair coordinates $(\theta_d, p_d)$; and
for each point y of interest, coherently combine the received datasets by weighting the datasets according to respective beamforming weights $w_d(y)=\omega(\theta_d, p_d; y)$, based on said respective detector pair coordinates $(\theta_d, p_d)$ and coordinates of said each point y of interest, so as to obtain a signal focusing on said each point y.

* * * * *